(12) United States Patent
Oh et al.

(10) Patent No.: US 6,498,421 B1
(45) Date of Patent: Dec. 24, 2002

(54) ULTRASONIC DRILLING DEVICE WITH ARC-SHAPED PROBE

(75) Inventors: Jisoo Oh, Lake Forest, CA (US); Ben Hur, Arcadia, CA (US)

(73) Assignee: Amega Lab, L.L.C., Lake Forest, CA (US)

( * ) Notice: Subject to any disclaimer, the term of this patent is extended or adjusted under 35 U.S.C. 154(b) by 43 days.

(21) Appl. No.: 09/882,495

(22) Filed: Jun. 15, 2001

(51) Int. Cl.[7] ................................................. H02N 2/00

(52) U.S. Cl. ............................ 310/323.18; 310/323.12; 310/323.19; 606/80

(58) Field of Search ....................... 310/323.18, 323.19, 310/323.12; 606/79, 80, 180; 604/22

(56) References Cited

U.S. PATENT DOCUMENTS

| | | | | |
|---|---|---|---|---|
| 3,569,748 A | * | 3/1971 | Minchenko et al. ... | 310/323.19 |
| 6,204,592 B1 | * | 3/2001 | Hur ........................ | 310/323.12 |

* cited by examiner

Primary Examiner—Gregory Huson
Assistant Examiner—Tuan Nguyen
(74) Attorney, Agent, or Firm—Drummond & Duckworth

(57) ABSTRACT

An ultrasonic suture device is provided for drilling arc shaped holes through hard materials, such as metals, glass, or bone. The ultrasonic suture device includes a transducer, horn and probe. The probe is constructed of three sections including a stem section, extension section and arc section. The stem section extends along the longitudinal axis of the ultrasonic suture device, while the arc section is constructed in the shape of an arc of a circle and is positioned concentrically with the stem's axis. At the distal extremity of the probe is a tip constructed for drilling into hard materials.

8 Claims, 3 Drawing Sheets

ULTRASONIC DRILLING DEVICE WITH ARC-SHAPED PROBE

BACKGROUND OF THE INVENTION

The present invention relates to ultrasonic drilling apparatus for highly efficient and precision use, such as medical and dental surgery. The present invention also relates to suturing devices for the medical field.

Dental and surgical procedures involving the use of an ultrasonic probe for removing tissue or for drilling are well known. For example, in dentistry various ultrasonic probes having operative tips that are caused to vibrate at a frequency of about 30,000 Hz are applied to the teeth and vibrated to remove scale and plaque from tooth surfaces. Ultrasonic probes are also used during cataract lens eye surgery to efficiently remove the cataract lens from the eye. Moreover, various surgical procedures make use of a ultrasonic probe for use in drilling holes through bone. Surgical procedures typically make use of various ultrasonic probes having operative tips that are caused to vibrate at frequencies between 20,000 Hz and 60,000 Hz with a stroke of about 20 $\mu$m to 150 $\mu$m depending on the medical purpose.

Meanwhile, health practitioners frequently use sutures to close various openings such as cuts, punctures, and incisions in various places in the human body. Sutures are also used to join two body parts together by attaching a suture to a first internal body part and then securing the suture to another body part. For example, reattachment of a rotator-cup tendon requires that a suture be passed through a detached tendon and then secured to a hole or anchor in a bone.

Sewing of sutures has been done previously by physicians with devices such as mandibular awls and J-hooks. A J-hook is a suture tool having a longitudinally extending handle, a stem projecting from the handle, and a hook projecting in the plane perpendicular to the axis of the handle and stem. The hook is rotated to push or pull the suture through a hole in the body tissue. Unfortunately, a J-hook tool cannot be used in connection with suturing through holes drilled in bone by prior art ultrasonic probes as the arc shaped end of the J-hook is incapable of projecting through the straight bore drilled by an ultrasonic probe.

It would thus be desirable to have an ultrasonic drilling device that drilled arced shapes through hard materials such as bone for medical procedures. It would also be desirable to provide an ultrasonic drill which was capable of drilling arced shapes through other hard materials such as boron carbide, glass, titanium carbide, steel and the like.

SUMMARY OF THE INVENTION

Briefly, in accordance with the invention, we provide an "ultrasonic suture device" capable of drilling arc shapes through hard materials. The ultrasonic suture device includes a piezoelectric transducer for converting an externally supplied electrical wave to an ultrasonic mechanical wave producing a mechanical longitudinal stroke. The ultrasonic suture device further includes a horn adjacent to the piezoelectric transducer. Either an exponential horn or stepped horn can be used depending on the device's purpose. The elongate horn has a proximal end and a distal end. The proximal end is positioned adjacent to the transducer, while the distal end forms an operative tip. The length of the elongate horn is determined by the equation $(\lambda/2)n$, where $\lambda$=wavelength and n=1, 2, 3, 4 . . . , to bring a nodal point to the distal end of the horn.

Attached to the distal end of the elongate horn is a probe. The probe includes a stem section which extends along a first axis. The probe further includes an extension section and an arc section. The arc section is semicircular in construction and positioned in the plane perpendicular to the stem's axis. Meanwhile, the extension section connects the stem section of the probe with the arc section of the probe. Preferably, the extension section first projects outwardly from the stem section's axis to define a first segment. Thereafter, the extension section transitions so as to have a small spiral segment in the plane perpendicular to the stem section's axis. Extending from the distal extremity of the extension section's spiral segment is the probe's arc section. Preferably, the arc section of the probe is semicircular in construction and also constructed in the plane perpendicular to the stem's axis. The length of the probe is determined by the equation $\lambda(2n+1)/4$, where $\lambda$=wavelength, and n=1, 2, 3 . . . to bring the maximum amplitude of the stroke to the distal end of probe.

In a preferred embodiment, the length of the ultrasonic suture device's elements are constructed dependant upon the wavelength ($\lambda$) produced by the transducer so that the sum of the lengths of the horn and probe is evenly divisible by $\frac{1}{4}\lambda$, but not evenly divisible by $\frac{1}{2}\lambda$ according to the equation $(\lambda/2)n+\lambda(2n+1)/4$ so that the maximum amplitude of the wave produced by the transducer is provided at the distal end of the probe. For example, in a preferred embodiment, the horn is one-half($\frac{1}{2}$) $\lambda$ in length, the stem section is one-half($\frac{1}{2}$) $\lambda$ in length, the first segment of the extension section is one-eighth ($\frac{1}{8}$) $\lambda$ in length, the second spiral segment of the extension section is one-eighth ($\frac{1}{8}$) $\lambda$ in length, and the length of the arc section is one-half ($\frac{1}{8}$) $\lambda$. As described, the sum of the lengths of the horn and probe is $\frac{7}{4}\lambda$, and thus evenly divisible by $\frac{1}{4}\lambda$ but not $\frac{1}{2}\lambda$. As understood by those skilled in the art the length is constructed to produce maximum vibration at the tip of the probe as maximum vibration is found at increments of one-half ($\frac{1}{2}$) $\lambda$ along the length of the probe from the point $\frac{1}{4}\lambda$ after the first nodal point after the transducer.

The wavelength is dependent on the frequency of the transducer and the velocity of the wave through the horn and probe. The transducer may produce any frequency for purposes of the present invention, though common ultrasonic frequencies of 20–60 kHz are considered preferable. The speed that the wave travels through the ultrasonic suture device will vary depending on the construction and materials used for the horn and probe. However, it has been found that if medical grade stainless steel is used, the wave speed through the device is approximately 5–6,000 m/second, and stainless steel SS316 has a velocity of 6,000 m/second. By using relatively simple mathematics, one skilled in the art can determine the wave length of the ultrasonic suture device by knowing the frequency of the device's transducer. For example, where a preferred ultrasonic suture device employs a stainless steel SS316 horn and probe, and a transducer producing 40 kHz, the wave length is equal to 6,000 m/second÷40 kHz (waves/second)=150 mm. Thus, the preferred ultrasonic suture device described above, having a transducer producing 40 kHz and having a horn and probe constructed of stainless steel SS316, has a horn length of 75 mm, and a probe having a stem length of 75 mm, a first extension segment of 18.75 mm, a second spiral extension segment of 18.75 mm, and an arc section having a length of 75 mm. Of course, the frequency of the transducer, material and the lengths of individual components may be altered by those skilled in the art without departing from the spirit and scope of the invention.

In operation, a person attempting to create an arc shaped bore in a hard material places the probe's tip adjacent to the hard material's exterior surface. The probe is then rotated about the stem section's axis so that the tip projects into the hard material along the arced path created by the arced construction of the arc section of the probe. The energy produced by the transducer is amplified by the horn and transmitted to the device's tip causing an arc shaped bore to be formed in the hard material as the probe is rotated.

The probe and arc section of the probe may be rotated by manually rotating the transducer, horn and probe with one's hands. Alternatively, the ultrasonic suture device of the present invention may include a construction wherein the transducer and horn are rotatably affixed within a housing as described in U.S. Pat. No. 6,204,592 which is incorporated by reference herein. The housing includes a separate electrical motor electrically coupled to a control system for controllably rotating the transducer and horn within the housing. Selective activation of the motor causes the transducer and horn to rotate within the housing, thereby causing the probe to rotate relative to the stem's axis.

Accordingly, it is a principal object of the invention to provide an ultrasonic device capable of producing arc shaped bores through hard materials.

It is still another object of the invention to provide an ultrasonic suture device for producing arc shaped bores through bone capable of being used in connection with suturing procedures.

These and other, further and more specific objects and advantages of the invention will be apparent to those skilled in the art from the following detailed description taken in conjunction with the drawings.

DETAILED DESCRIPTION OF THE INVENTION

Figure 1:
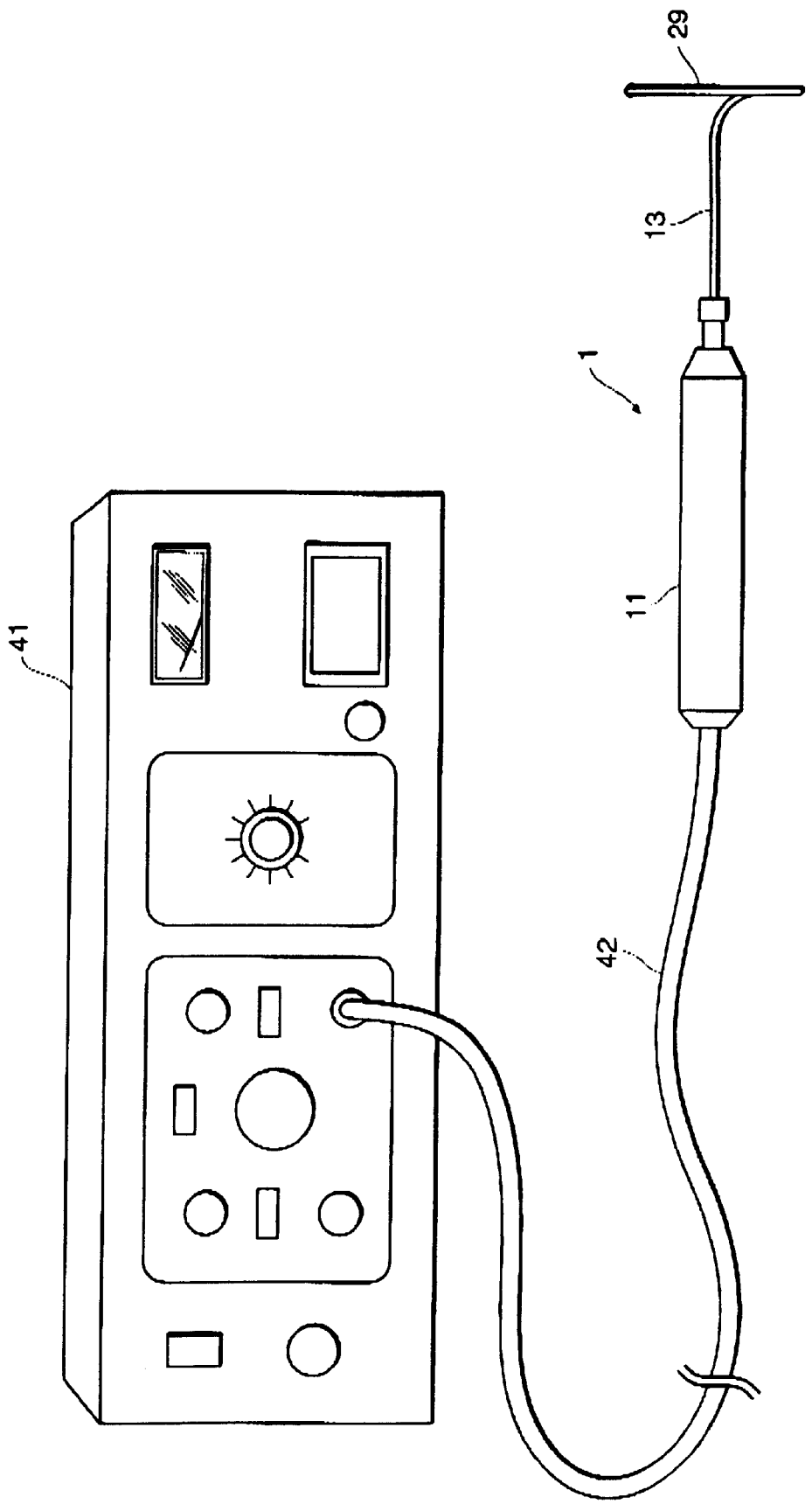
FIG. 1 is a not-to-scale elevational view illustrating the various components of the ultrasonic suture device of the present invention.

While the present invention is susceptible of embodiment in various forms, as shown in the drawings, hereinafter will be described the presently preferred embodiments of the invention with the understanding that the present disclosure is to be considered as an exemplification of the invention, and it is not intended to limit the invention to the specific embodiments illustrated.

Figure 2:
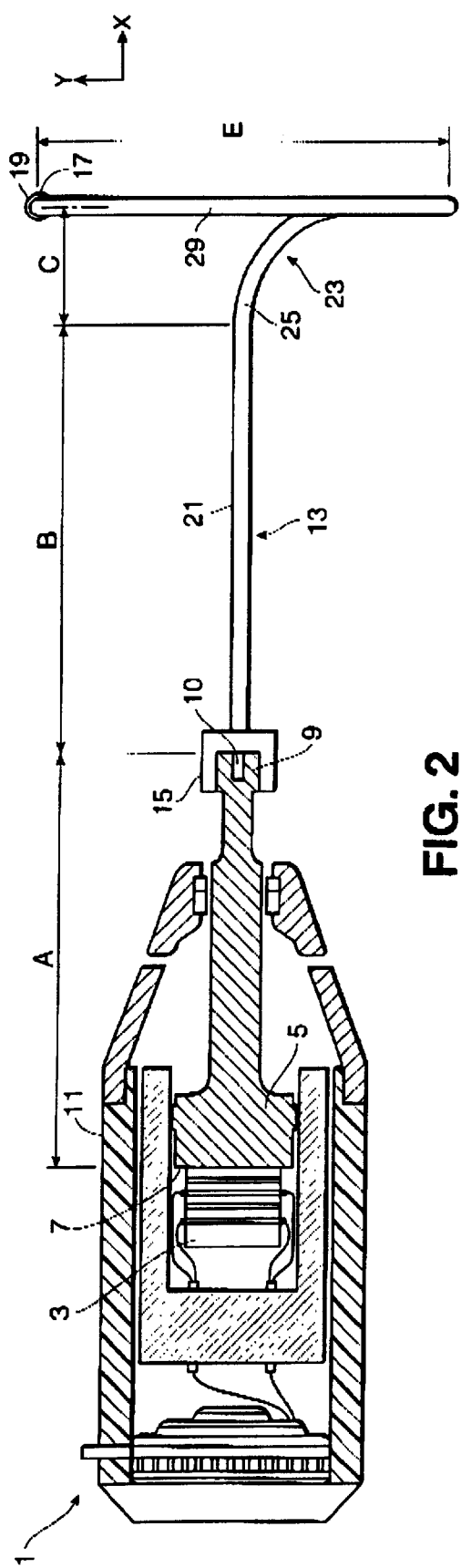
FIG. 2 is a cross-sectional top view illustrating the handle portion of the ultrasonic suture device and a top view of the probe of the ultrasonic suture device of the present invention.

As shown in FIGS. 1 and 2, the ultrasonic suture device 1 of the present invention includes a piezoelectric transducer 3 connected to a generator 41. The generator produces an electrical wave which travels along electrical cable 42 to the piezoelectric transducer which produces a high frequency sonic vibration. Preferably, the piezoelectric transducer is constructed as a BLT (Bolt-clamped Langevin Type Transducer) with PZT (Piezoelectric Lead Zirconate Titanate Crystals).

The ultrasonic suture device also includes an elongate horn 5 having a proximal end 7 and a distal end 9. The proximal end 7 is positioned adjacent to the transducer 3, and preferably the transducer has an axial bore so that the proximal end 7 of the horn projects into the axial bore of the transducer. Attaching the horn to the transducer through an axial bore has been found to help transmit vibration from the transducer to the elongate horn. Preferably, the manufacturing tolerances for attaching the horn to the transducer are extremely small to reduce any dampening of the ultrasonic vibration produced by the transducer. The elongate horn may be either an exponential horn or stepped horn depending on the ultrasonic suture device's purpose. Exponential horns have a low-Q (quality factor) and a wider resonating frequency range, while a stepped horn has a high-Q and relatively high gain (amplitude).

The ultrasonic suture device also includes a housing 11 for housing both the transducer 3 and a portion of the horn 5. The distal end 9 of the horn projects out of the housing. Preferably, the housing is elongate in construction and sized to be easily controlled and positioned by a technician's hand. Depending on the use of the ultrasonic suture device of the present invention, the transducer and horn may be rotatably mounted within the housing so as to rotate about the horn's longitudinal axis. Moreover, a motor (not shown) may be provided within the housing to selectively control the rotation of the transducer 3 and horn 5 relative to the housing 11. For the best performance, the housing should include self-lubricating bearings as described in U.S. Pat. No. 6,204,592.

Of importance to practicing the present invention, attached to the distal extremity 9 of the horn 5 is a probe 13. The probe's 13 proximal end 15 attaches to the distal end of the horn by a threaded connection 10. Contrary to the relatively straight probes of the prior art, the probe 13 of the present invention includes three distinct sections and a tip 19 at the distal end 17 of the probe. More particularly, the probe 13 includes a stem section 21, an extension section 23 and an arc section 29.

Figure 4:
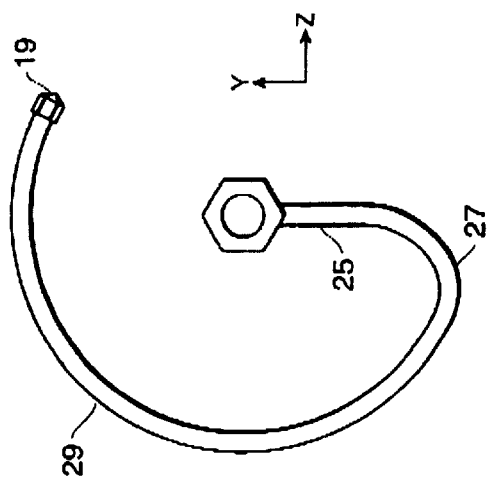
FIG. 4 is a bottom view of the probe shown in FIG. 3.
Figure 3:
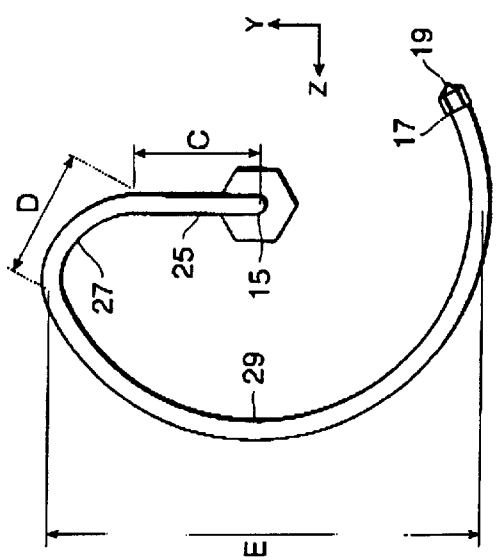
FIG. 3 is a top view illustrating a right-hand rotating probe for use with the ultrasonic suture device of the present invention.

The construction of the probe is best explained in connection with the Cartesian coordinate system shown in the FIGS. 2–4 which define axis x, y, and z, and planes xy, yz and xz. The probe's stem section 21 is a straight segment defining a stem axis, which as shown in the figures is coincident with the x axis. Meanwhile, the extension section 23 includes a first segment 25 and a second short spiral segment 27 which, in combination, provides a transition from the stem section 21 to the arc section 29. The first segment 25 projects away from the x axis, which as shown in the figures continues substantially within the xy plane. Once the projection has formed a 90° bend, the first segment 25 transitions into the spiral segment 27. Preferably, the spiral segment 27 is constructed within the yz plane, which is perpendicular to the stem section's axis. Extending from the distal end of the spiral segment 27 is the arc section 29. The arc section 29 of the probe 13 is shaped like an arc of a circle and preferably extends 135° to 180° of a circle. Also preferable, the arc section 29 is positioned concentric with the stem section 21 so that rotation of the ultrasonic suture device 1 about its longitudinal axis will cause the arc section to rotate in the path of a circle. More particularly, the extension section 23 provides a transition linkage between the stem section 21 and arc section 29 which concentrically positions the arc section 29 so as to track a circular path when the ultrasonic suture device is rotated.

The probe 13 may be constructed of various materials, though stainless steel medical grades are considered advisable. Moreover, where the ultrasonic suture device is to be used in connection with medical surgery, it is preferred that the arc length be 2 to 10 cm in length and the diameter of the probe be 0.5 to 2.0 mm so that standard suture threads may be employed.

Figure 7:
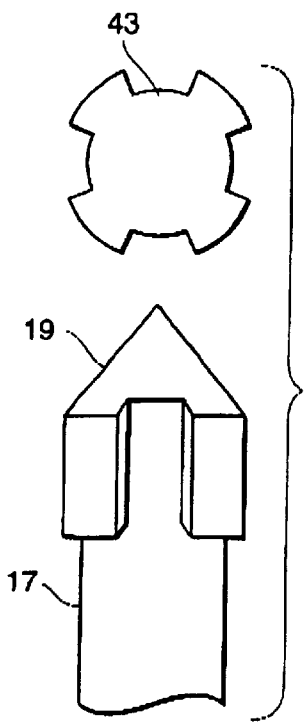
FIG. 7 is a side view of a tip that can be used with the ultrasonic suture device of the present invention.
Figure 8:
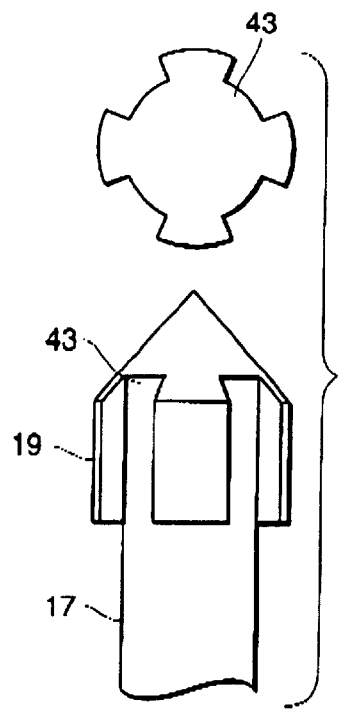
FIG. 8 is a rotated side view of the tip shown in FIG. 7.

At the distal extremity of the probe 13 is the tip 19. The tip may be attached to the end of the probe by numerous means known to those skilled in the art, such as by a threaded connection. The operative tip can take any form designed for ultrasonic machines. For example, the tip can be constructed as a flat screwdriver tip, a phillips head tip or even as a conventional drill bit. Preferably, the tip is made of a high strength material such as stainless steel or a metal alloy. As shown in FIGS. 7 and 8, preferably the tip 19 includes longitudinal slots 43 for allowing drilled material to pass through the slots. Moreover, it is preferred that the tip have a slightly larger diameter than the probe so as to drill a slightly larger hole through a desired material than the cross-section of the probe to provide sufficient space between the probe and the bore's sidewalls for debris to evacuate during the drilling procedure.

Preferably, the lengths of the elongate horn 5 and probe 13 are determined by the length of a wavelength $\lambda$ in accordance with the equations $\lambda/2(n)+\lambda(2n+1)/4$ to maximize the amplitude of the axial stroke produced by the transducer 3. With reference to FIGS. 2–4, in a preferred embodiment the length of the horn A is equal to one-half (½) $\lambda$, the length of the stem section B of the probe is one-half (½) $\lambda$, the length of the first segment C of the extension section is one-eighth (⅛) $\lambda$, the length of the second spiral section D is one-eighth (⅛) $\lambda$ and the length of the arc section is one-half (½) $\lambda$. The frequency produced by the transducer and materials of the horn and probe effect the velocity of the ultrasonic waves transmitted through the ultrasonic suture devices. For example, an ultrasonic suture device having a transducer operating at 40 kHz, and including a horn and probe constructed of stainless steel SS316, providing a velocity of 6,000 m/second, the wavelength is 150 mm. Thus, a preferred ultrasonic transducer 1 of the present invention having a transducer operating at 40 kHz and a horn and probe constructed of SS316, the horn would have a length of 75 mm; the stem would have a length of 75 mm; the first extension segment would have a length of 18.75 mm; the second extension segment would have a length of 18.75 mm; and the arc section would have a length of 75 mm. Of course, these dimensions may be altered without departing from the spirit and scope of the invention. For example, providing a stem length of one (1) $\lambda$ (150 mm), instead of one-half (½) $\lambda$ (75 mm), would still provide a horn and probe length divisible by one-half (½) $\lambda$ thus providing maximum ultrasonic energy at the tip of the probe.

Figure 5:
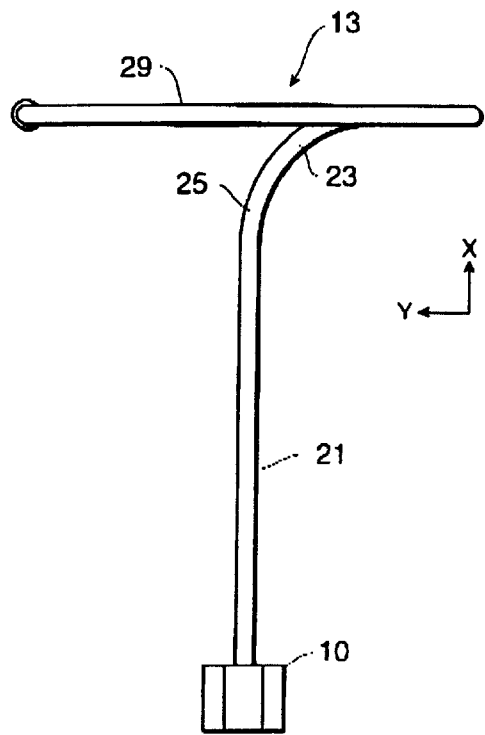
FIG. 5 is a side view of a left-hand rotating probe for use with the ultrasonic suture device of the present invention.
Figure 6:
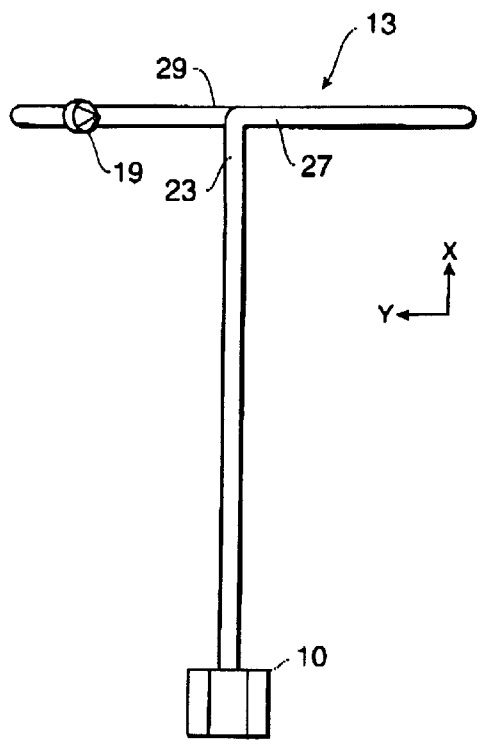
FIG. 6 is a side view of a right-hand rotating probe for use with the ultrasonic suture device of the present invention.

Although the present invention has been described with reference to the preferred embodiments, workers skilled in the art will recognize that changes may be made in form and detail without departing from the spirit and scope of the invention. For example, the probe may be constructed with an arc section having either right handed rotation as shown in FIGS. 3, 4 and 6, or the probe may be constructed with an arc section having left handed rotation as shown in FIGS. 1, 2 and 5. Therefore, the scope of the invention shall not be limited by the specification above.

Having described our invention in such terms to enable those skilled in the art to make and use it, and having identified the presently preferred embodiments thereof, we claim:

1. An ultrasonic drilling device comprising:

a hollow housing;

a transducer positioned within said housing;

an elongate horn having a proximal end engaging said transducer and a distal end; and a probe engaging said distal end of said elongate horn and positioned at least partially external to said housing, said probe including a stem section defining a first axis, an extension section, an arc section and a tip, said arc section being adjacent to said tip and shaped like the arc of a circle, said arc section and tip are positioned in a plane substantially perpendicular to said first axis.

2. The ultrasonic drilling device of claim 1 wherein said arc section is positioned concentric with said first axis.

3. The ultrasonic drilling device of claim 1 wherein said arc section is semicircular.

4. The ultrasonic drilling device of claim 1 wherein said probe further includes an extension section, said extension section being at least partially helical or spiral in construction.

5. The ultrasonic drilling device of claim 1 wherein said probe is rotatable relative to said housing.

6. The ultrasonic drilling device of claim 1 wherein said transducer and horn create an ultrasonic wave having a wavelength $\lambda$, said arc section having a length of approximately (½$\lambda$) n, where n=1, 2, 3 . . . .

7. The ultrasonic drilling device of claim 1 wherein said transducer, horn and probe create an ultrasonic wave having a wavelength $\lambda$, said sum of the lengths of said horn and said probe being approximately evenly divisible by one-fourth (¼) $\lambda$, but not one-half (½) $\lambda$.

8. The ultrasonic drilling device of claim 1 wherein said transducer, horn and probe create an ultrasonic wave having a wavelength $\lambda$, said horn having a length of approximately one-half (½) $\lambda$, said stem section having a length of approximately one-half (½) $\lambda$, said extension section having a length of approximately one-quarter (¼) $\lambda$, and said arc section having a length of approximately one-half (½) $\lambda$.

* * * * *